United States Patent
Quintessenza

(10) Patent No.: US 7,320,705 B2
(45) Date of Patent: Jan. 22, 2008

(54) BICUSPID PULMONARY HEART VALVE AND METHOD FOR MAKING SAME

(76) Inventor: James Quintessenza, 6101 - 54 St. South, St. Petersburg, FL (US) 33715

( * ) Notice: Subject to any disclaimer, the term of this patent is extended or adjusted under 35 U.S.C. 154(b) by 43 days.

(21) Appl. No.: 11/041,603

(22) Filed: Jan. 24, 2005

(65) Prior Publication Data
US 2006/0167542 A1     Jul. 27, 2006

Related U.S. Application Data

(60) Provisional application No. 60/538,870, filed on Jan. 23, 2004.

(51) Int. Cl.
*A61F 2/24* (2006.01)
(52) U.S. Cl. .................................... 623/2.12
(58) Field of Classification Search ........ 623/2.1–2.24, 623/1.24
See application file for complete search history.

(56) References Cited

U.S. PATENT DOCUMENTS

| | | | |
|---|---|---|---|
| 2,922,437 A * | 1/1960 | Rippingilla | ................. 137/844 |
| 4,340,977 A | 7/1982 | Brownlee et al. | |
| 4,790,844 A | 12/1988 | Ovil | |
| 5,344,442 A * | 9/1994 | Deac | ......................... 623/2.12 |
| 5,500,015 A | 3/1996 | Deac | |
| 5,824,063 A * | 10/1998 | Cox | ........................... 623/2.1 |
| 6,299,637 B1 | 10/2001 | Shaolian et al. | |
| 6,517,576 B2 * | 2/2003 | Gabbay | ..................... 623/2.14 |
| 6,673,109 B2 * | 1/2004 | Cox | ........................... 623/2.12 |
| 6,682,559 B2 | 1/2004 | Myers et al. | |
| 6,752,828 B2 * | 6/2004 | Thornton | ................... 623/1.24 |
| 6,875,230 B1 * | 4/2005 | Morita et al. | .............. 623/2.12 |
| 7,163,556 B2 * | 1/2007 | Xie et al. | ................... 623/2.14 |
| 2003/0163194 A1 | 8/2003 | Quijano et al. | |
| 2003/0163195 A1 | 8/2003 | Quijano et al. | |
| 2003/0181974 A1 * | 9/2003 | Xie et al. | ................... 623/1.24 |
| 2004/0138742 A1 * | 7/2004 | Myers et al. | .............. 623/2.12 |
| 2005/0149181 A1 * | 7/2005 | Eberhardt | ................... 623/2.14 |
| 2006/0235511 A1 * | 10/2006 | Osborne | ..................... 623/2.12 |
| 2006/0253188 A1 * | 11/2006 | Case | .......................... 623/1.24 |
| 2007/0050014 A1 * | 3/2007 | Johnson | ..................... 623/1.24 |

* cited by examiner

*Primary Examiner*—Suzette Gherbi
(74) *Attorney, Agent, or Firm*—Squire Sanders & Dempsey, LLP

(57) ABSTRACT

A heart valve constructed from a synthetic resin that is designed to be surgically implanted in the right ventricular outflow tract of the heart, comprising a plurality of flexible members, and an orifice.

9 Claims, 14 Drawing Sheets

BICUSPID PULMONARY HEART VALVE AND METHOD FOR MAKING SAME

RELATED APPLICATIONS

This is a non-provisional application claiming the benefit of U.S. provisional patent application Ser. No. 60/538,870 on Jan. 23, 2004, the entire contents of which is incorporated herein by reference.

BACKGROUND OF THE INVENTION

This invention relates generally to a tubular heart valve having a plurality of flexible members that are open when at rest, but capable of collapsing to prevent reverse flow, and more particularly to a pulmonary heart valve comprising a bicuspid configuration, and made from a safe, relatively inexpensive, effective, and durable material, such as a fluoropolymer like PTFE sold under trademarks such as Teflon® and GORE-TEX®, or other synthetic resin suitable for use in biologic applications. The present invention provides a safe, relatively inexpensive, easily-constructed, effective and durable option for patients in need of right ventricular outflow tract reconstruction.

Many patients who have had surgical reconstruction of the right ventricular outflow tract come back to the doctor in need of reoperative surgical reconstruction of the right ventricular outflow tract (RVOT). Typically there is a history of previously operated tetralogy of Fallot (TOF) or pulmonary stenosis (PS). Tetralogy of Fallot is a heart problem that is characterized by four defects in the heart: 1) ventricular septal defect (VSD), which is a hole between the two bottom chambers of the heart; 2) pulmonary stenosis, or a narrowing at or slightly below the pulmonary valve; 3) positioning of the aorta over the ventricular septal defect; and 4) the right ventricle being unusually muscular.

The predominant physiologic abnormality is pulmonary insufficiency (PI), but varying degrees of RVOT obstruction may also be present. It is generally believed that patients tolerate PI reasonably well. In some, however, the long term effects of PI and subsequent right ventricle (RV) enlargement and dysfunction result in poor exercise tolerance and increased incidence of arrhythmias. Numerous surgical options are available for these patients; however, the optimal timing and specific valve used for reconstruction remain uncertain. Less than ideal experience with heterograft RVOT reconstruction stimulated interest into alternative materials and techniques. Favorable experimental and clinical experience with reconstruction using PTFE monocusp valves spurred an interest to consider a new method of reconstruction with this material.

Increasingly, over the last several years, concerns regarding post-operative pulmonary insufficiency or insufficiency/stenosis have emerged. The previous adage that pulmonary insufficiency after valvectomy and/or transanular patching during repair of TOF was well-tolerated is now being questioned. Recent studies with more refined methods of evaluation utilizing echocardiogram or magnetic resonance imaging (MRI), as well as exercise testing, clearly show there is a relationship between pulmonary insufficiency and volume overload that results in right ventricular enlargement and dysfunction. Symptoms resulting from physical exertion are late and usually follow these objective changes in ventricular dysfunction and size. Additionally, life threatening ventricular arrhythmias seem to be associated with the more severe cases of pulmonary insufficiency and ventricular changes.

There is good evidence that RV enlargement and dysfunction is reversible following pulmonary valve replacement (PVR). However, recent evidence shows that there is a lack of significant recovery of RV indices following PVR in adults with long-standing pulmonary insufficiency. Therefore, the timing of PVR is of major importance in the overall maintenance of ventricular function and optimal long-term outcomes. Additionally, a program of aggressive PVR in conjunction with intraoperative cryoblation is effective in reducing both the size of the heart chamber and the potential for lethal arrhythmias in TOF patients with severe pulmonary insufficiency. It is also useful in decreasing the QRS duration, wherein "QRS" is a complex of waves on an echocardiogram that represent the time it takes for the ventricles to depolarize—the normal length of time being between 40 milliseconds and 160 milliseconds. In general, indications for PVR are evolving but currently include patients with moderate-severe PI/PS and 1) exertional symptoms, class II or greater, 2) RV systolic dysfunction and/or enlargement, 3) decreased exercise tolerance 4) ventricular arrhythmias and/or QRS duration greater than 160 milliseconds.

There is considerable debate as to what type of valve or reconstruction is optimal for the pulmonary position. A vast array of materials and methods have been utilized. Recent studies support the use of homografts, replacement valves from human donors, as well as stented and unstented heterograft valves, valves from non-human donors (pig valves are commonly used). However, despite definite early patient improvement, all reports for use of biologic valves show a significant incidence of recurrent valvar insufficiency and/or obstruction. A recent study of thirty-six patients utilizing homografts and heterografts for PVR noted that nine out of the thirty-four patients that were followed-up developed moderate to severe PI, and seventeen out of thirty-four developed significant obstruction within 80 months follow-up. Similarly, within 4.9 years, the incidence of homograft insufficiency was 50% mild, and 28% moderate-severe. Recent evidence suggests an immunologic basis for this early graft failure pattern.

In light of the above, it was thought that a non-immunologic, non-degenerating, and relatively durable material, such as PTFE, and a different method of insertion of the valve would provide more optimal results. Experience from 3-17 years utilizing a PTFE monocusp for RVOT reconstruction suggests reasonable long-term durability and freedom from degeneration. A larger study of 158 patients using a PTFE monocusp for RVOT reconstruction, with follow-up from 6 months to 8 years, demonstrated no stenosis, calcification, or embolization. There was, however, significant development of pulmonary insufficiency graded as moderate to severe by 35 months in this monocusp study.

The prior art discloses many types of heart valves, such in U.S. Pat. No. 5,344,442 issued to Deac, which discloses a cardiac valve designed to replace defective mitral valves in a patient's heart that comprises a plurality of flexible trapezoidal membranes each joined to another trapezoidal membrane to form a frustoconical annular body. Also, U.S. Pat. No. 4,340,977 issued to Brownlee, et al. for a catenary mitral valve replacement, which includes a mitral valve comprising a stent with a circular base and two upstanding, diametrically opposed struts that separate a pair of diametrically opposed arcuately shaped depressed reliefs. U.S. Pat. No. 5,500,015 issued to Deac for a cardiac valve comprising a plurality of membranes; U.S. Pat. No. 4,790,844 issued to Ovil, for a cardiac valve with an annular body having a bishop's miter shape with a cylindrical end and a pair of diametrically opposed triangular flap portions extending therefrom, and when the valve is inserted, the mitered end is free and the cylindrical end is attached to heart tissue; U.S. Patent Application Publication No. US2003/0181974 A1, filed by Xie, et al. for a bioprosthesis and method for suturelessly making same, which discloses a diamond-shaped frame to which a membrane is attached and wherein the frame is folded on itself and a slit cut into the folded side to allow fluid to flow through it; U.S. Pat. No. 6,685,559 B2, issued to Myers, et al. for a prosthetic heart valve that discloses a valve that includes a plurality of leaflets that are sewn together creating an annular structure which is then sutured into the heart; U.S. Patent Application Publication No. US2003/0163195 A1, filed by Quijano, et al. for a stentless atrioventricular heart valve fabricated from a singular flat membrane, which discloses attaching a membrane to a circumferential valve ring wherein the ring is sutured into an atrioventricular junction of a patient's heart.

SUMMARY OF THE INVENTION

The present invention provides a generally tubular heart valve with first and second ends, wherein the first end comprises an orifice of predetermined size and shape, defined by at least two opposing free edges of a predetermined length, and wherein the orifice can occupy either a first or second position, wherein the first position is flat and generally closed and the second position is open.

BRIEF DESCRIPTION OF THE DRAWINGS

A particularly preferred embodiment of the invention of this apparatus will be described in detail below in connection with the drawings in which.

DESCRIPTION OF PREFERRED EMBODIMENTS

Figure 1:
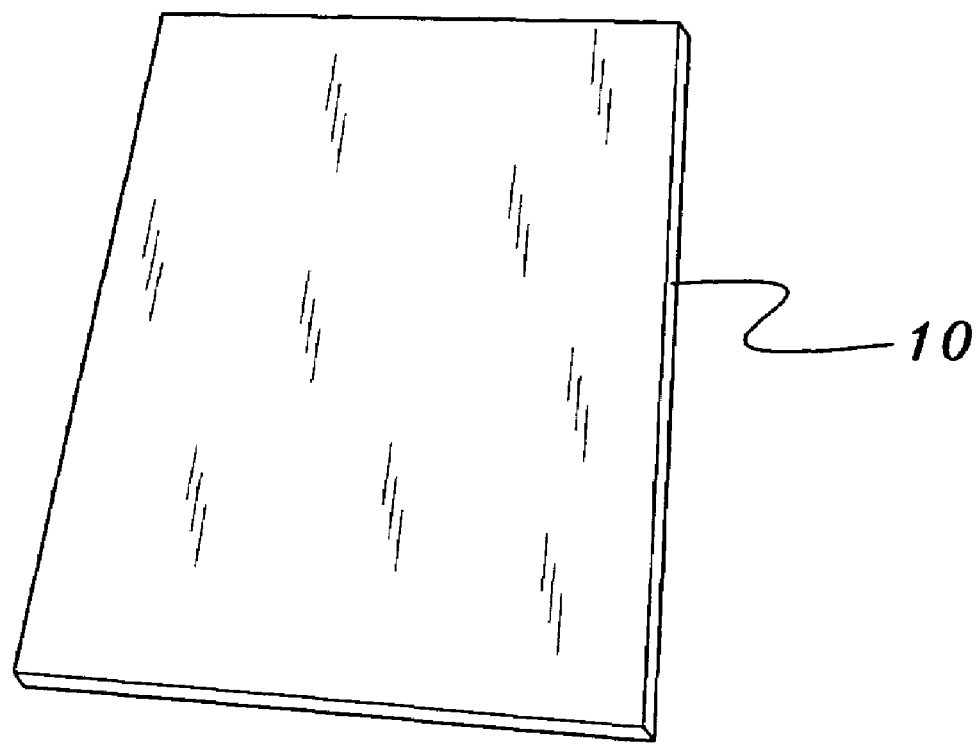
FIG. 1 is a flat sheet of PTFE material from which the a preferred embodiment will be crafted.

A particularly preferred embodiment of the present invention is illustrated in the drawings.

The preferred embodiment of the present invention comprises a heart valve that is constructed from a synthetic, non-degradable, durable, safe, material, such as a fluoropolymer like PTFE, GORE-TEX®, Teflon®, or other synthetic resin suitable for use in biologic applications, and a method for making and inserting the heart valve.

Figure 6:
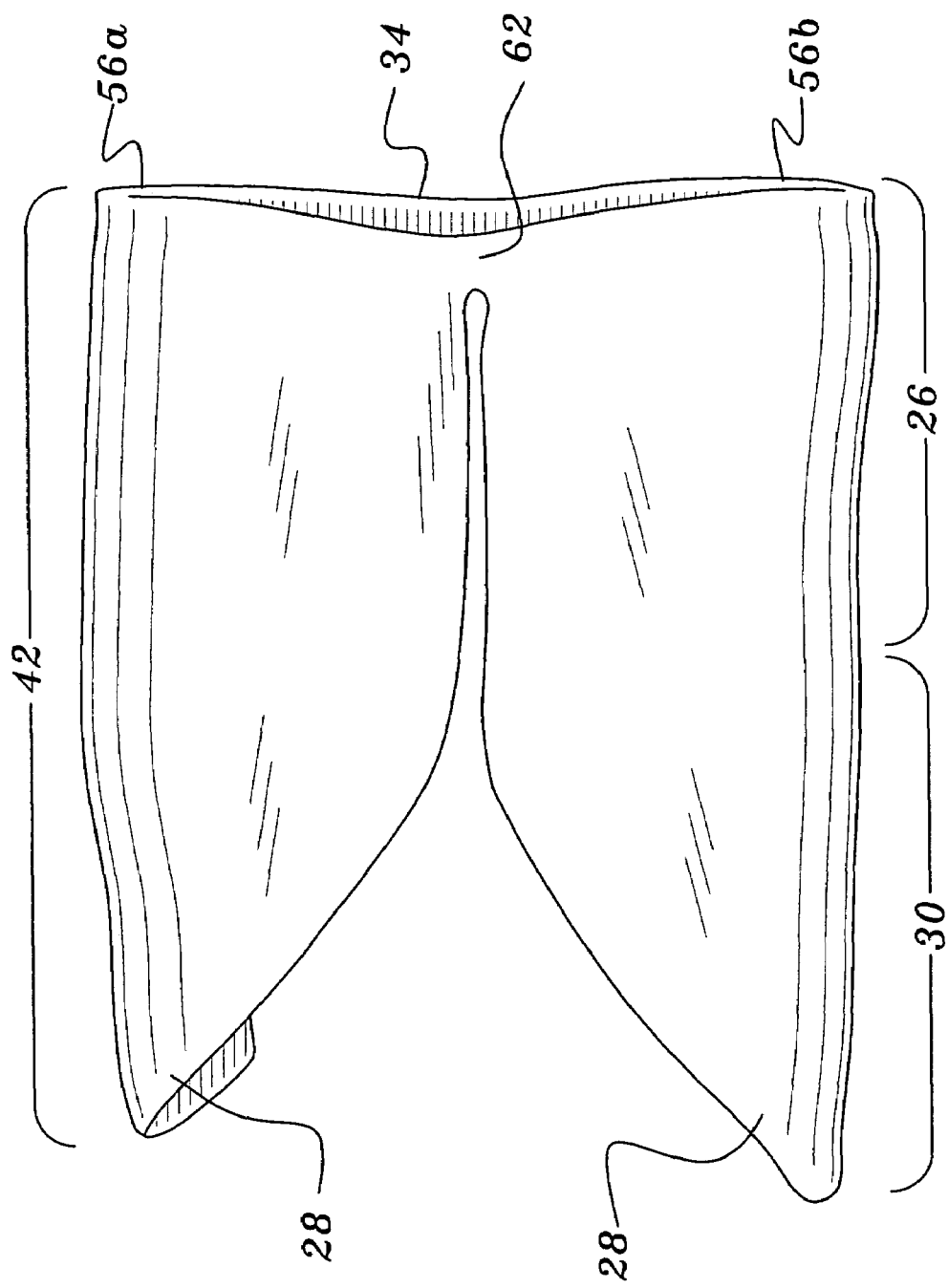
FIG. 6 shows a horizontal view of the preferred embodiment.
Figure 7:
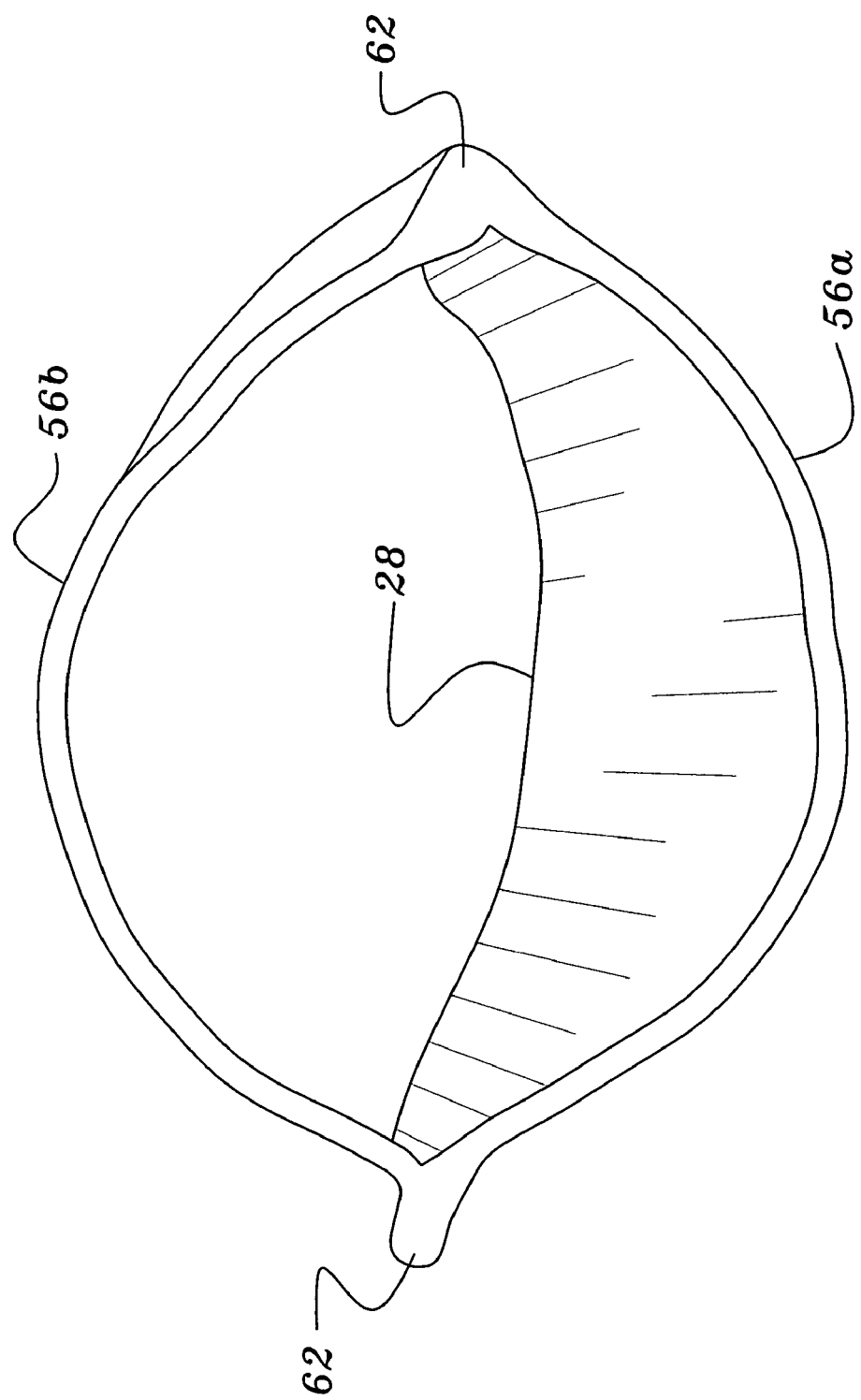
FIG. 7 shows a longitudinal view of the preferred embodiment.
Figure 8:
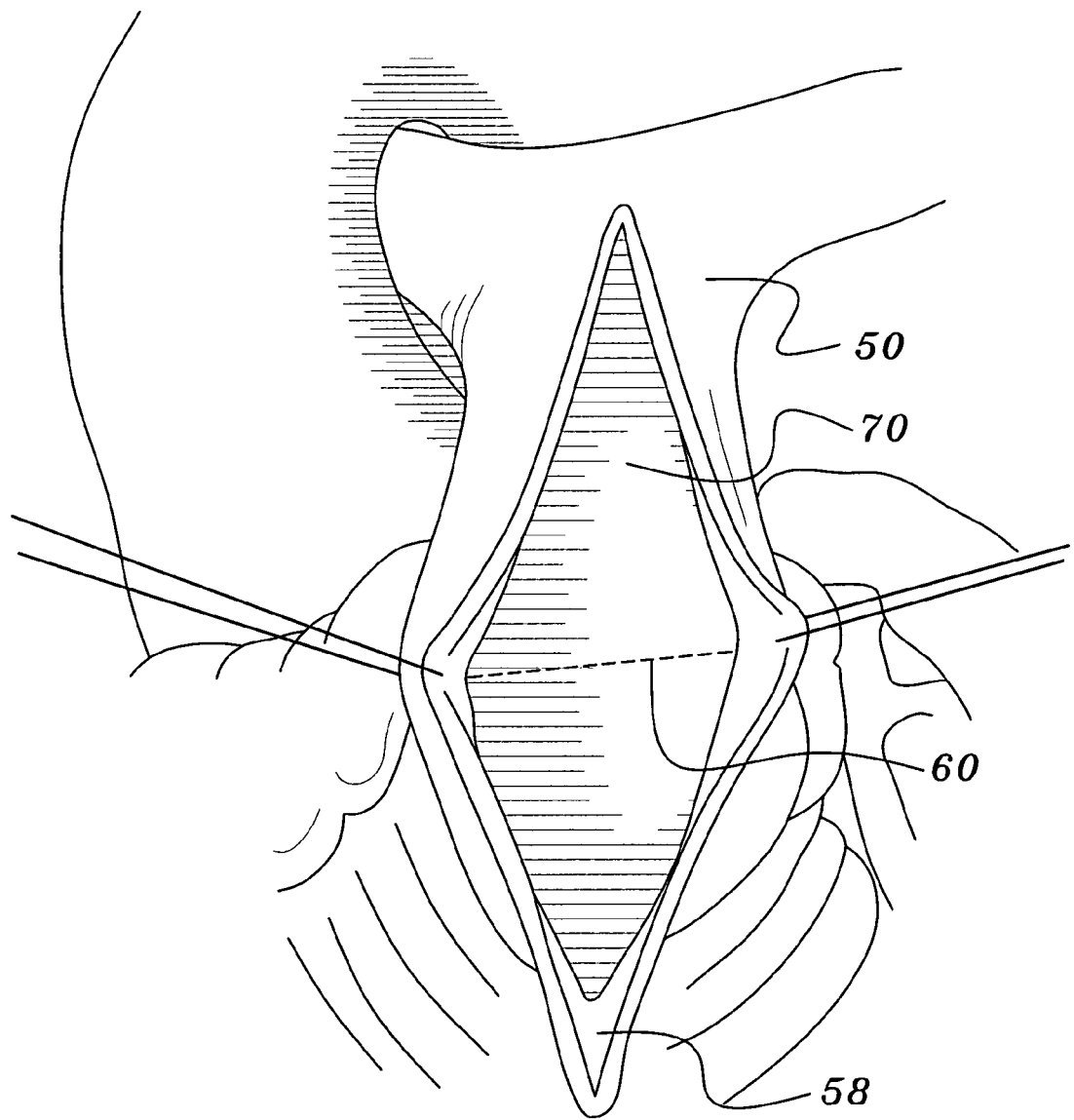
FIG. 8 depicts the incision in the right ventricular outflow tract into which the preferred embodiment will be inserted.
Figure 9:
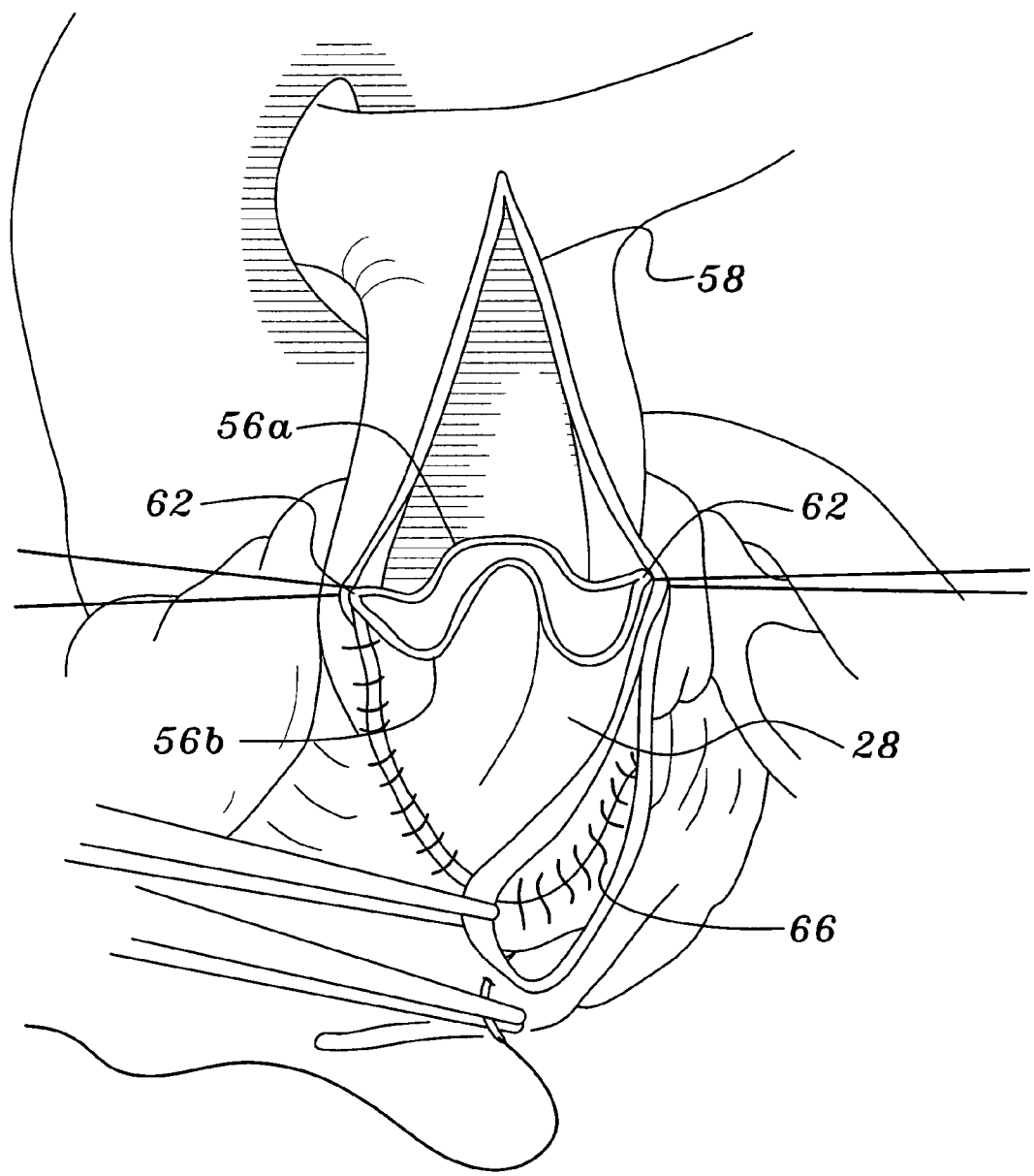
FIG. 9 depicts the preferred embodiment being sewn into place.
Figure 10:
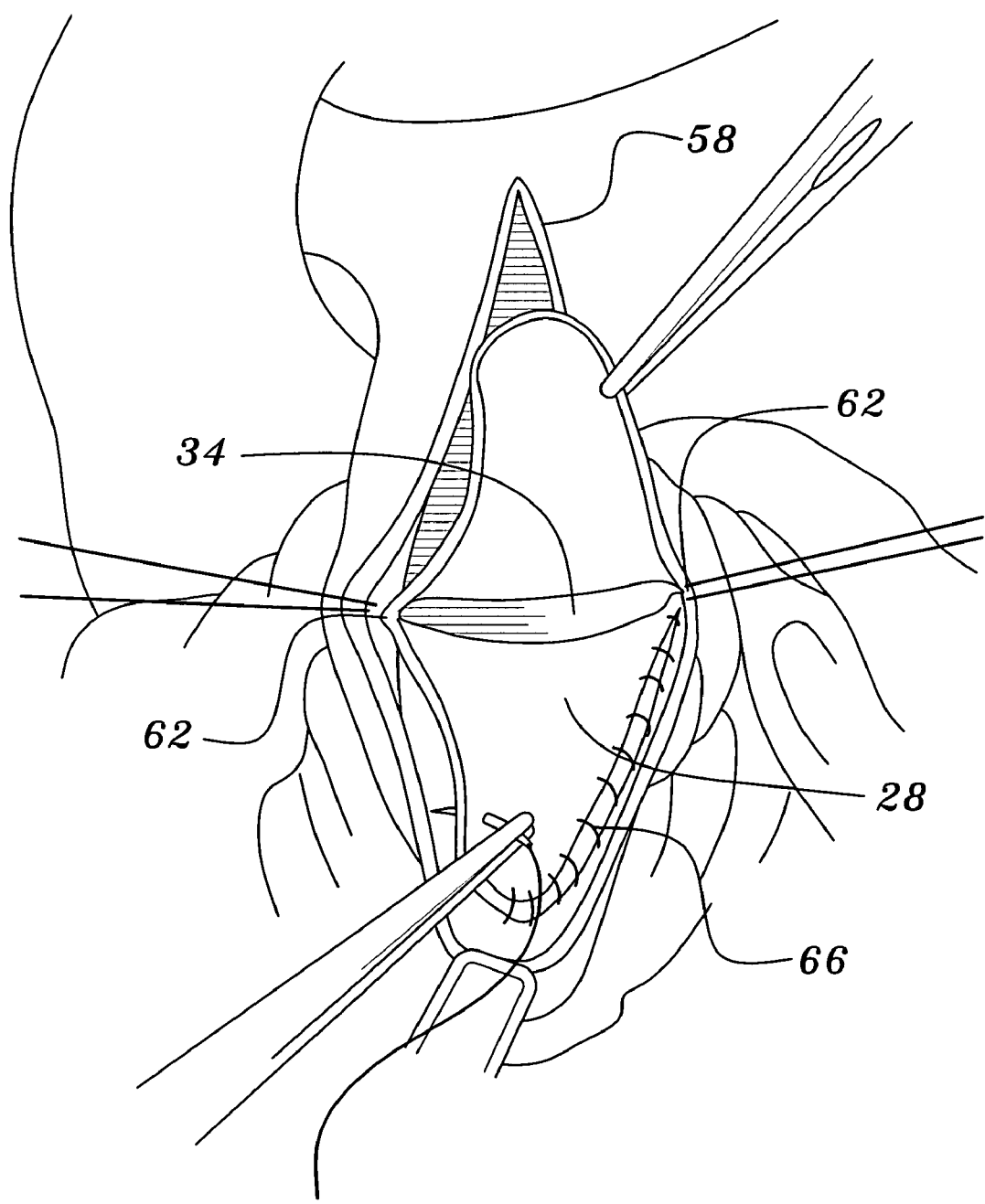
FIG. 10 depicts the preferred embodiment being sewn into place.
Figure 11:
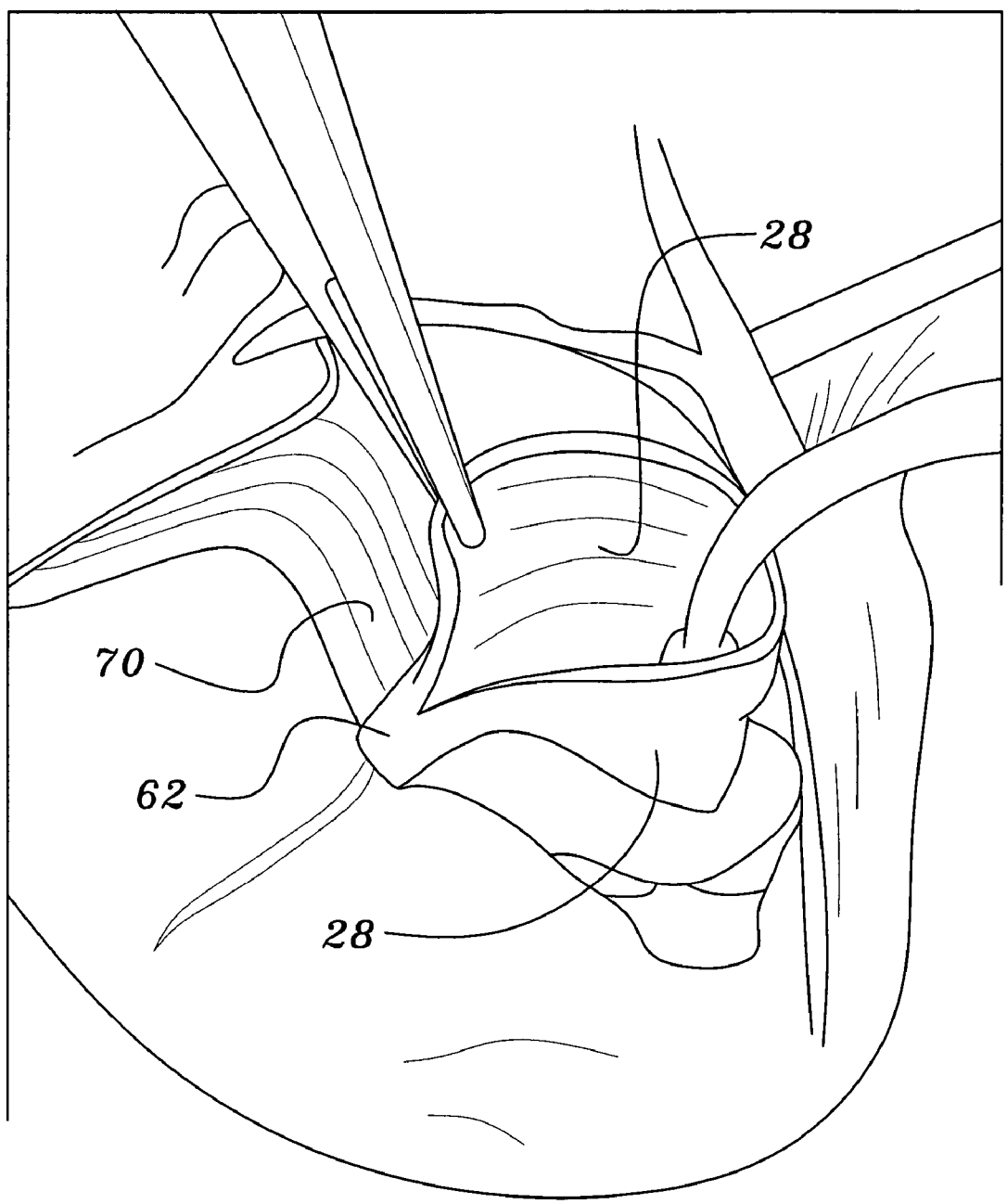
FIG. 11 shows the actual placement of the preferred embodiment into a heart while the valve is in the open position.
Figure 12:
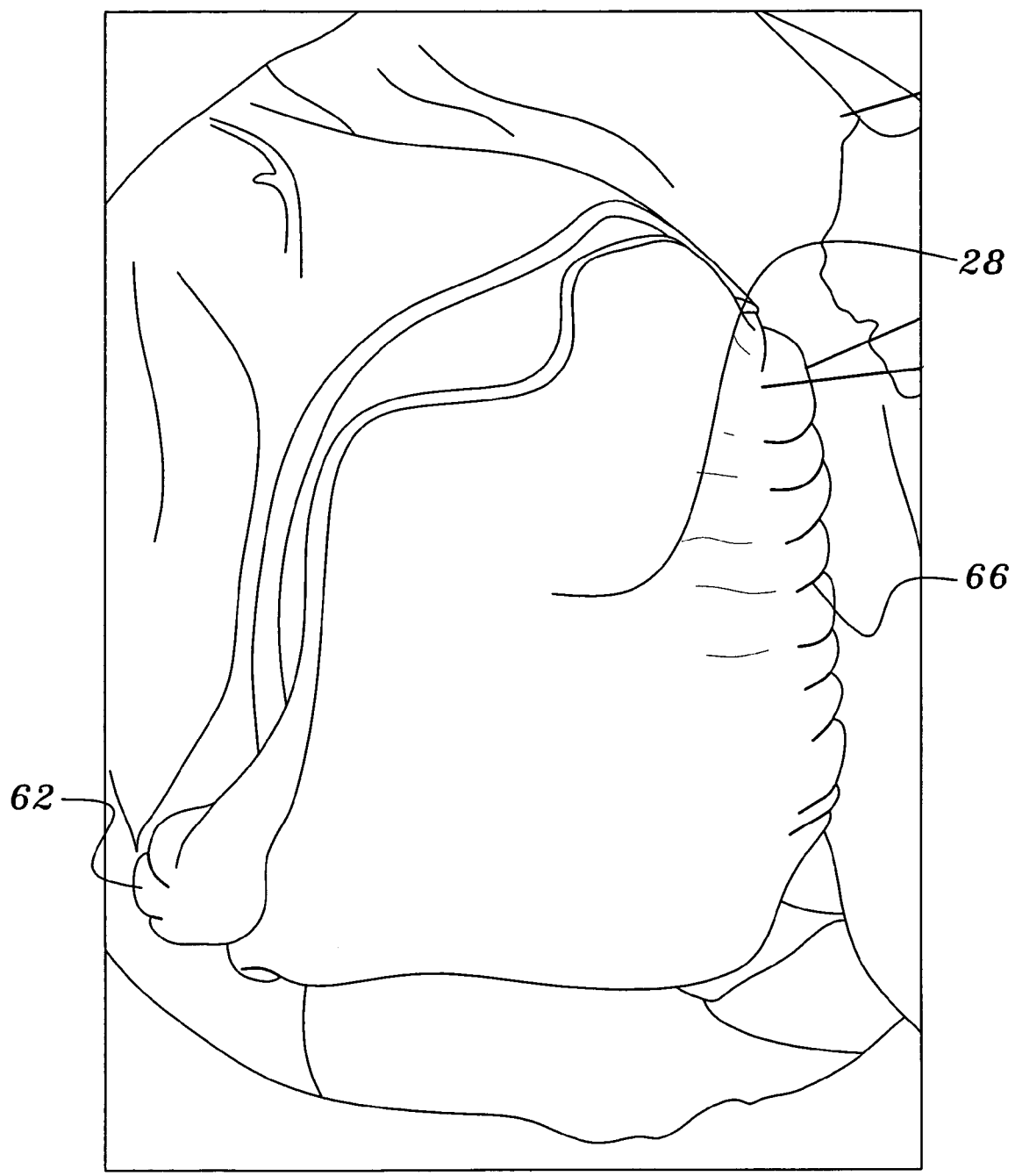
FIG. 12 shows the actual placement of the preferred embodiment into a heart while the valve is in the generally closed position.
Figure 13:
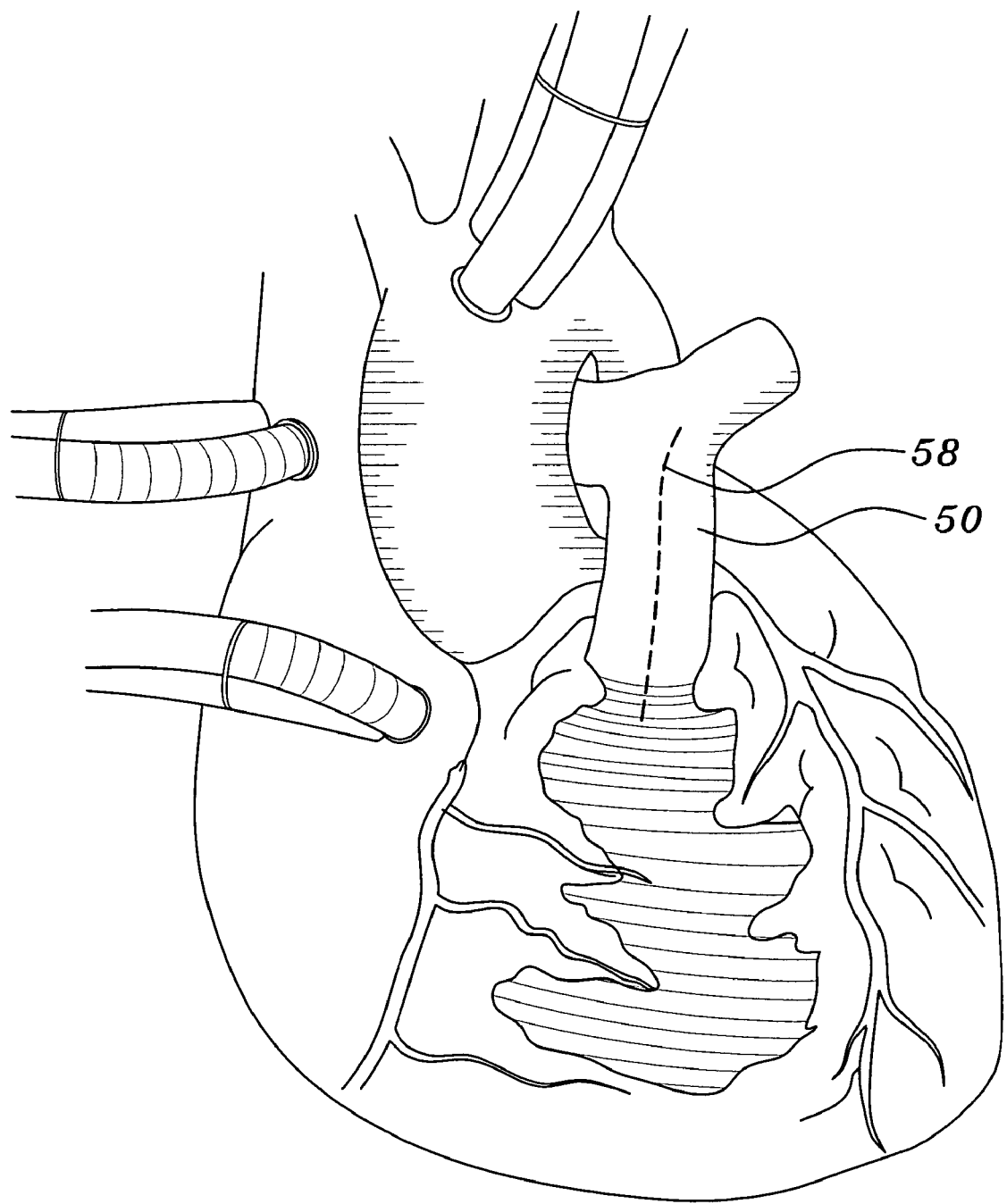
FIG. 13 is an illustration of the human heart, showing a dashed line where the incision into the right ventricular outflow tract is to be made.
Figure 14:
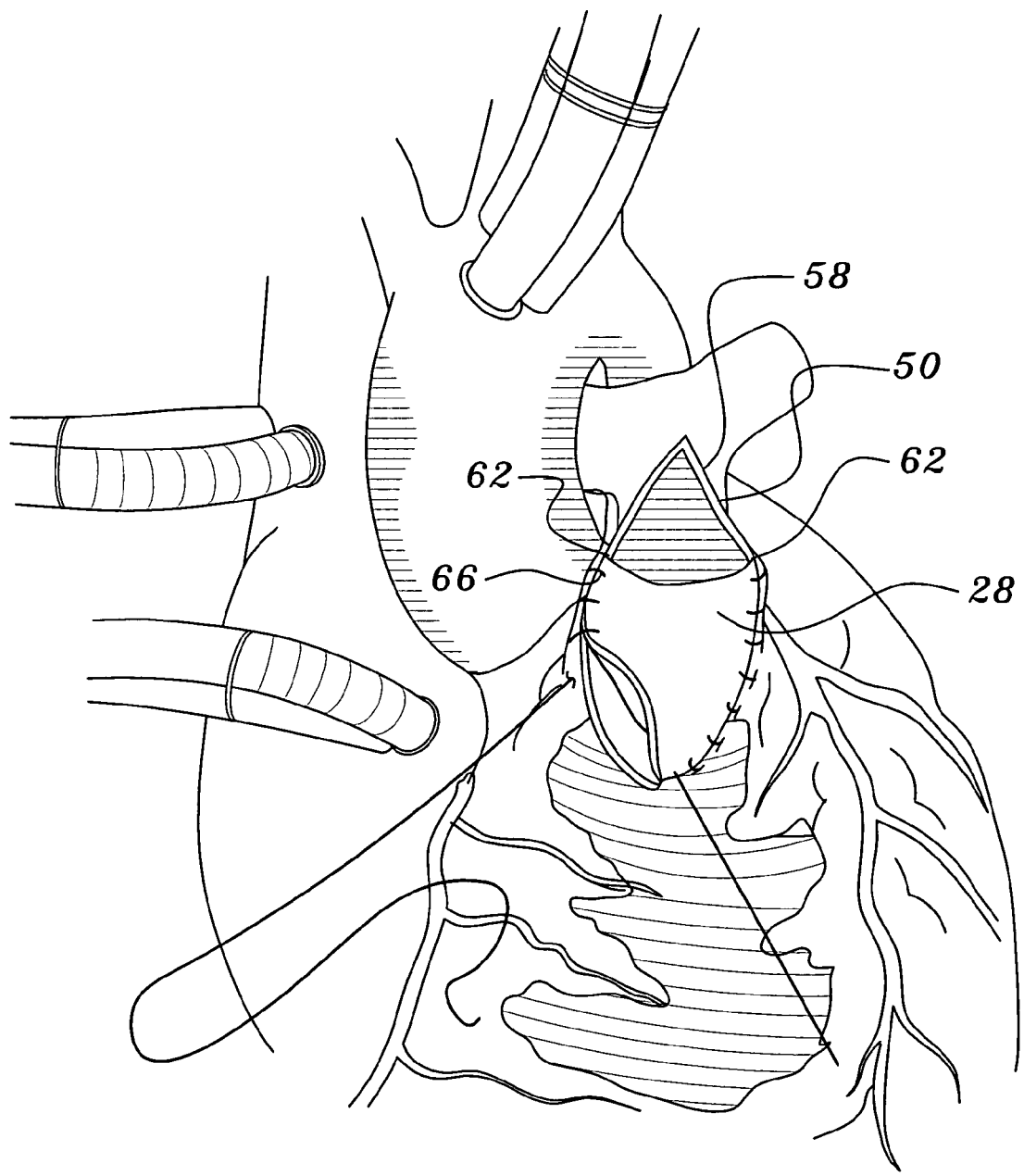
FIG. 14 is an illustration of the human heart into which the preferred embodiment is being sewn.

The preferred embodiment of the present invention is shown in FIGS. 6 and 7, and comprises a generally tubular element 42 with a first 26 and a second 30 end, wherein the first end 26 comprises a generally circular orifice 34 defined by at least two opposing free edges 56a, 56b of a predetermined length, and the second end 30 comprises a plurality of flexible members 28. Two flexible members 28 are shown in the figures. Further, the orifice 34 can occupy either of two positions, one being flat and generally closed (FIG. 12), the second being generally circular and open (FIG. 11). The predetermined length of the two opposing free edges 56a, 56b of the orifice 34 can be about 1.5 times the diameter 60 of a patient's right ventricular outflow tract 50.

Figure 2:
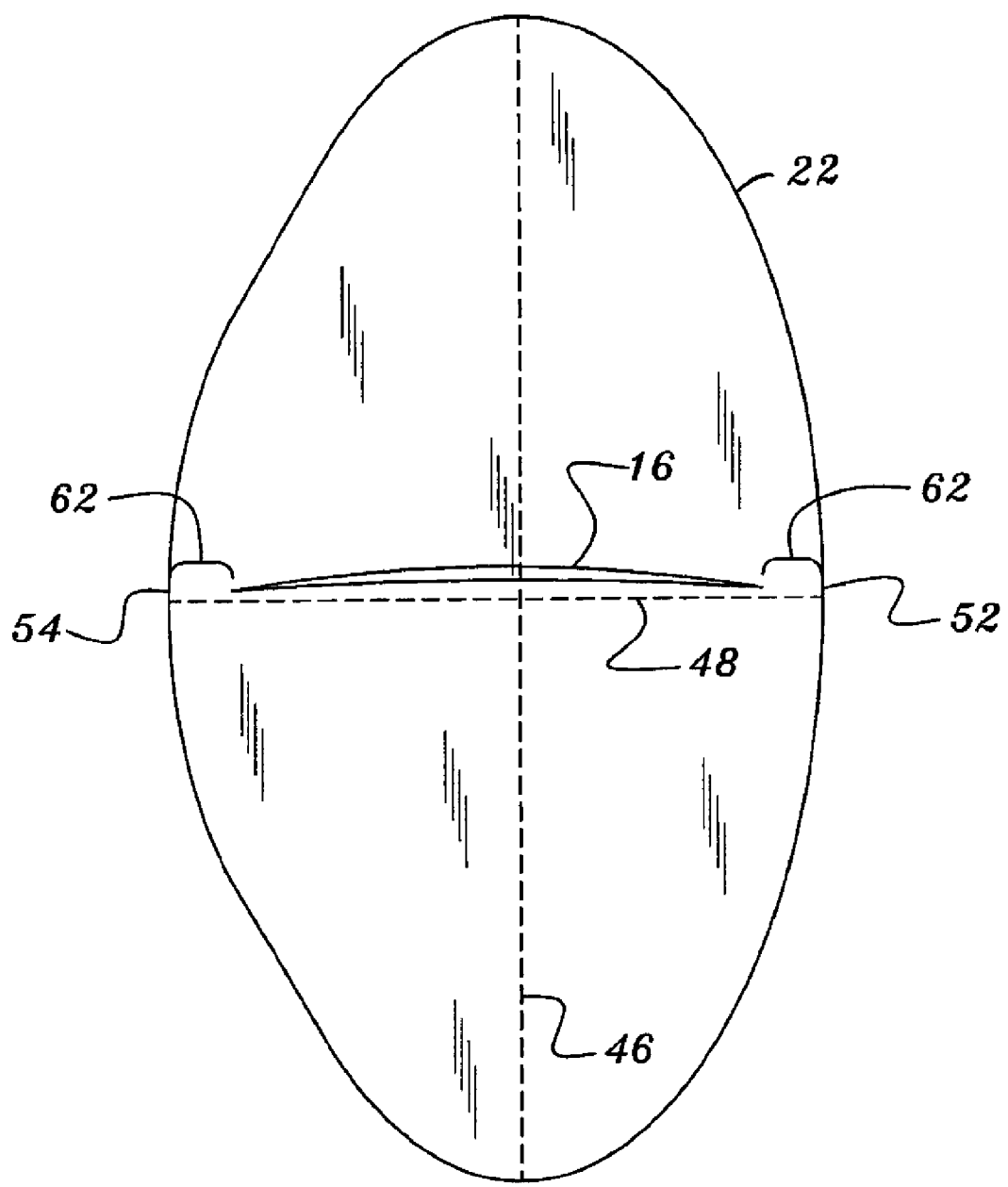
FIG. 2 is an ellipse that has been cut out from the flat sheet.

The present invention also encompasses a method of making the heart valve, shown in FIGS. 8-14, which comprises the steps of making an incision 58 into the right ventricular outflow tract 50 and measuring the diameter 60 of the right ventricular outflow tract. Then, from a flat sheet of synthetic resin 10 (FIG. 1), which may be a synthetic, non-degradable, durable, safe, material, such as a fluoropolymer like PTFE, GORE-TEX®, Teflon®, or other synthetic resin suitable for use in biologic applications, an ellipse 22 (FIG. 2), with a minor axis 48 and a major 46 axis, is cut. The minor axis 48 has a predetermined length and is defined by first 52 and second 54 edges, wherein the predetermined length should measure about 1.5 times the diameter 60 of the patient's right ventricular outflow tract 50, and be defined by two peripheral edges 62.

Figure 3:
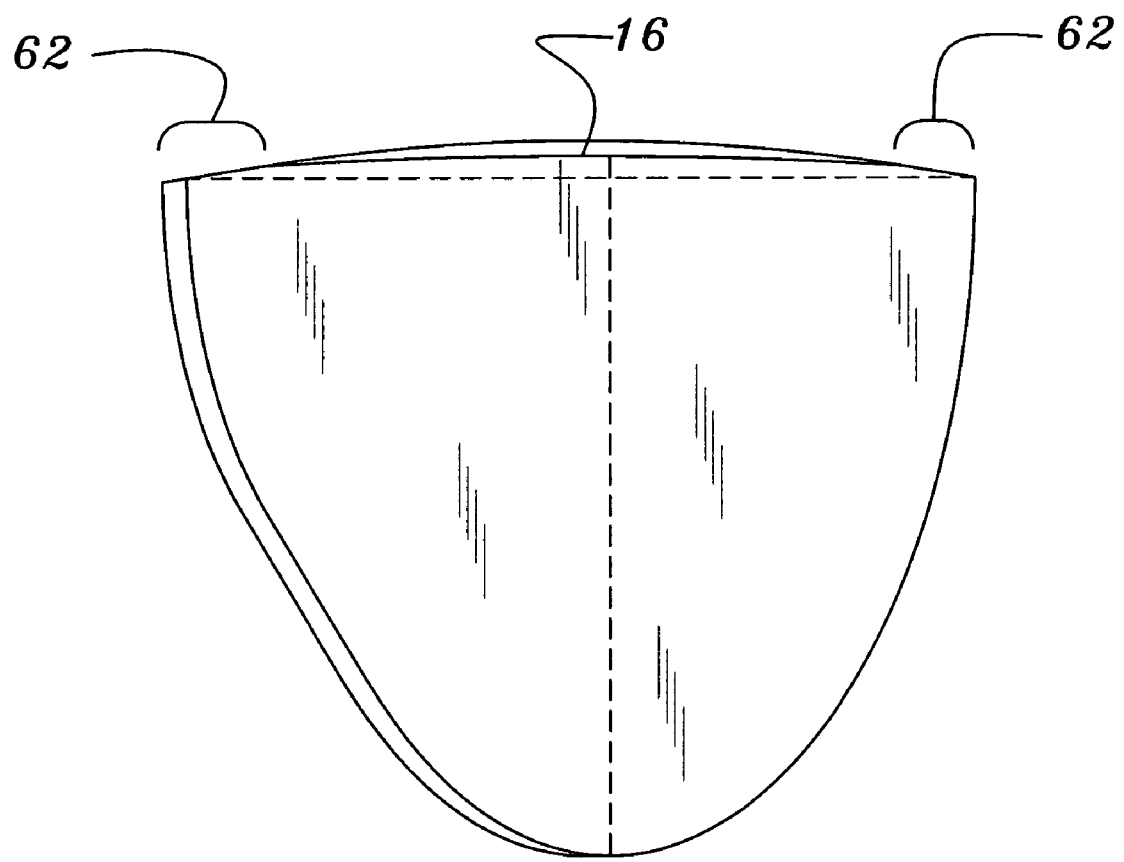
FIG. 3 is the ellipse, shown folded in half, with the fold defining one end.
Figure 4:
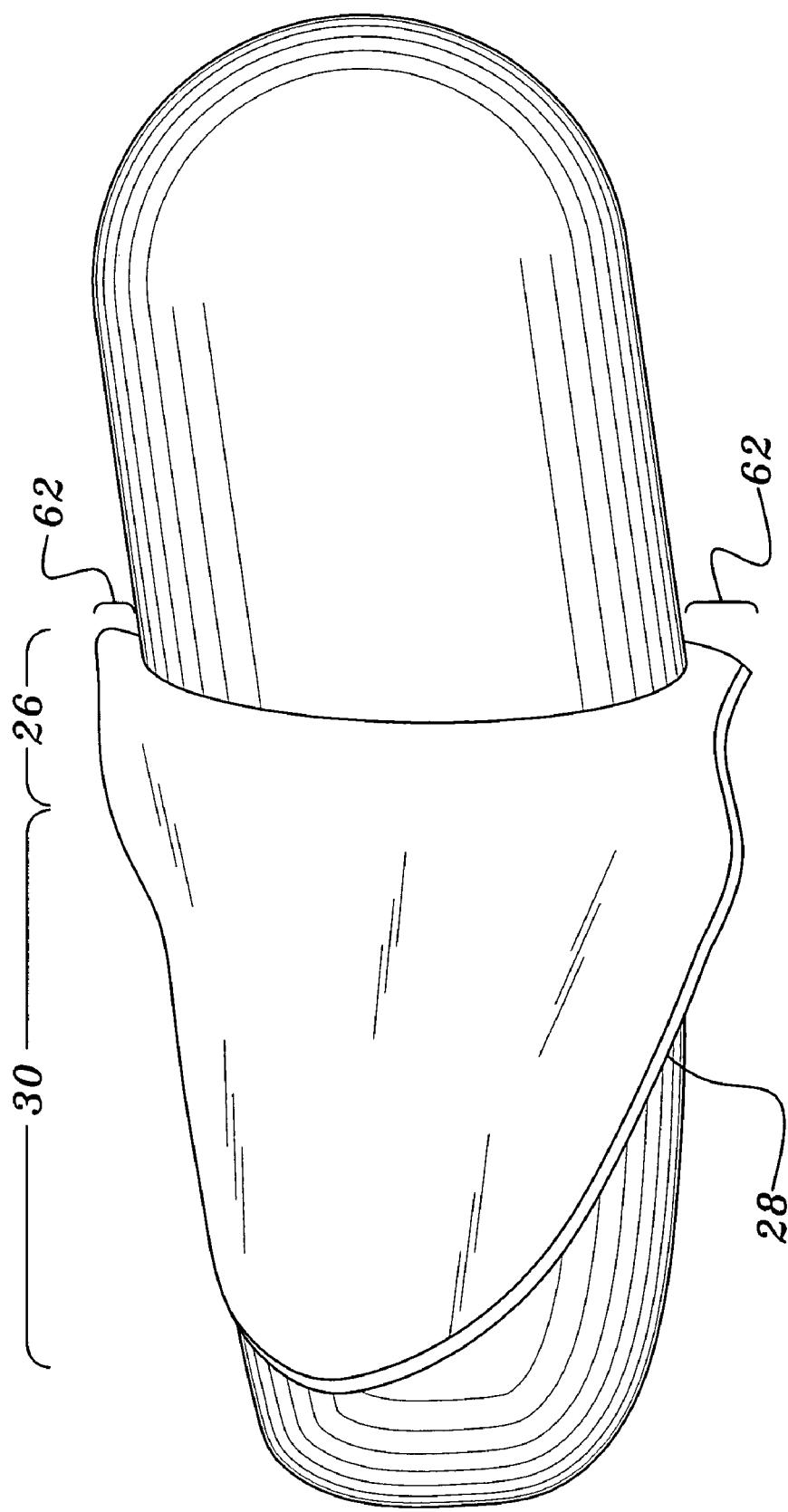
FIG. 4 is a top elevation a preferred embodiment being sized with a sizing tool.
Figure 5:
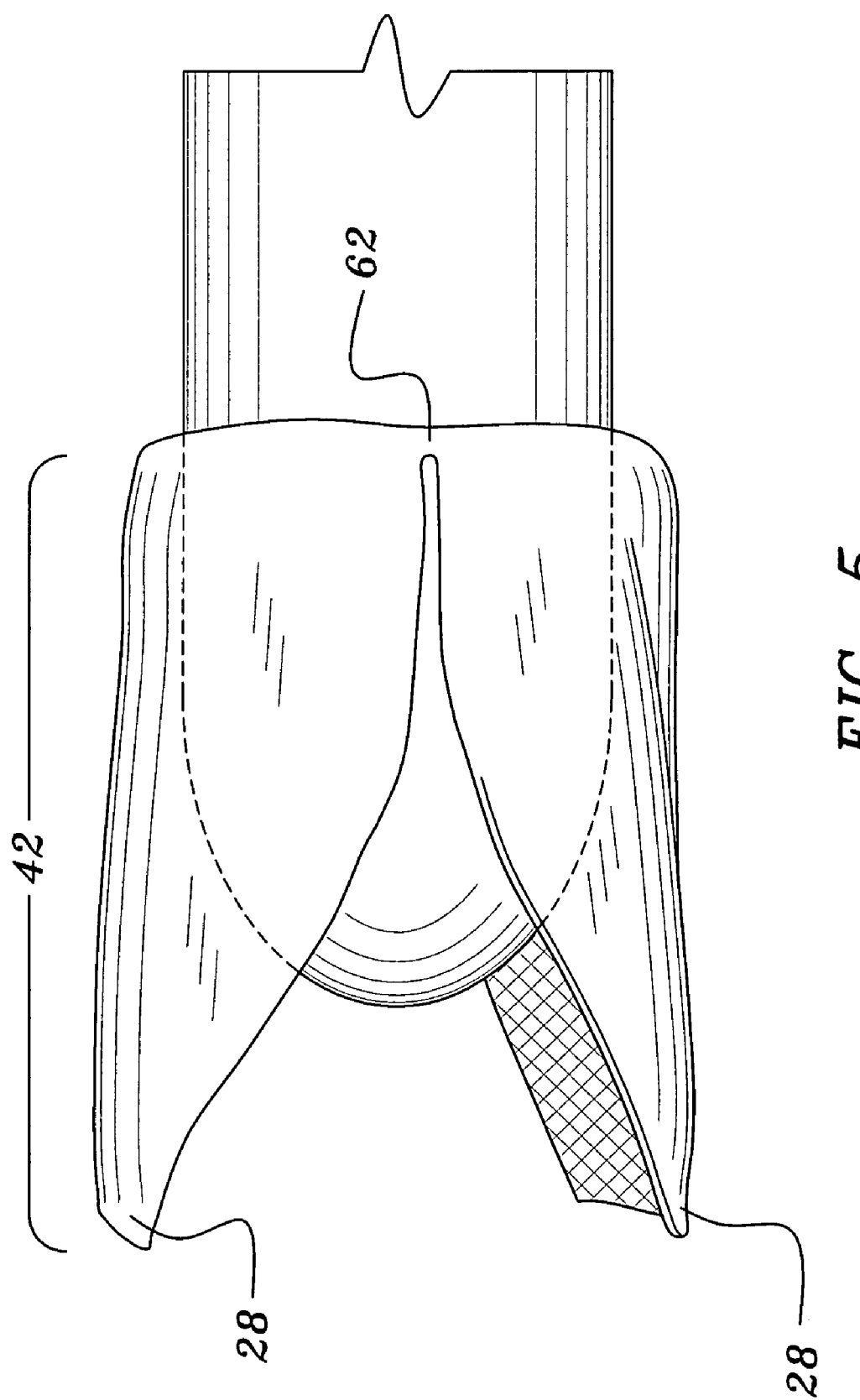
FIG. 5 is a side view of a preferred embodiment being sized with a sizing tool.

The ellipse 22 is then incised along the minor axis 48, such that the incision 16 extends along the minor axis 48, starting at about 2 mm from a first edge 52, and ending at about 2 mm from a second edge 54. The ellipse 22 is then folded in half on itself (FIG. 3) along the minor axis 48 such that the incision 16 may be formed (FIGS. 4-5) into a generally circular orifice 34 (FIGS. 6-7) of a predetermined size.

The invention also contemplates the insertion (FIGS. 8-14) of the heart valve into a patient's right ventricular outflow tract, comprising the steps of making an incision 58 in the right ventricular outflow tract 50 and attaching each of the flexible members 28, conveniently via sutures 66, to the anterior and posterior walls of the infundibular septum 70 of the right ventricular outflow tract 50, such that the flexible members 28 are generally parallel to each other, and such that a generally tubular configuration is maintained (FIG. 11).

When inserted into the patient's right ventricular outflow tract, the generally tubular configuration enables the incision to extend across the right ventricular outflow tract, such that the incision 16 can be formed into the generally circular orifice 34 when blood is flowing through the RVOT, and such that the incision 16 can close into the generally flat and closed position to prevent backflow as the blood flow ceases or slightly reverses as patient's heart beats. Thus, the heart valve has a generally one-way valve function. The flexible members 28 hold the heart valve in position, as they are sutured to the walls of the infundibular septum 70, and prevent it from becoming dislodged in use.

While the foregoing describes particularly a preferred embodiment of the method and apparatus of this invention, it is to be understood that this embodiment is illustrative only of the principles of this invention and is not to be considered limitative thereof. Because numerous variations and modification of the apparatus and method of this invention will readily occur to those skilled in the art, the scope of this invention is to be limited solely by the claims appended hereto.

What is claimed is:

1. A heart valve comprising:
   a generally tubular element with first and second ends;
   the first end comprising an orifice of a predetermined size and shape, and defined by at least two opposing free edges, wherein said orifice can occupy either a first or a second position, wherein said first position is flat and generally closed, and said second position is generally circular and open; and
   the second end comprising at least two flexible members, each of the flexible members including an edge region having no frame structure.

2. The heart valve of claim 1 wherein a length of said orifice between said at least two opposing free edges when said orifice is generally closed is equal to about 1.5 times the diameter of a patient's right ventricular outflow tract.

3. The heart valve of claim 1, wherein the tubular element is formed of a fluoropolymer.

4. The heart valve of claim 1, wherein the tubular element is formed of polytetrafluoroethylene.

5. The heart valve of claim 1, wherein the tubular element is formed of a biocompatible, synthetic resin.

6. A method of making a heart valve comprising the steps of:
   measuring the diameter of a patient's right ventricular outflow tract;
   cutting from a flat sheet of flexible synthetic resin an ellipse having a major and a minor axis, wherein the minor axis has a predetermined length and is defined by at least two peripheral edges;
   incising said ellipse along the minor axis, such that said incision extends along the minor axis for a distance approximately equal to 1.5 times the measured diameter of the patient's right ventricular outflow tract, and is defined by said at least two peripheral edges;
   folding said ellipse in half on itself along said minor axis; and
   forming said incision into an orifice of predetermined diameter and shape such that the flexible synthetic resin sheet forms a generally tubular shape with said incision at one end thereof forming an orifice that can open and close when inserted into the patient's right ventricular outflow tract.

7. The method of claim 6 wherein said at least two peripheral edges are each about 2 millimeters long.

8. A method of treating heart disease comprising the steps of:
   making an incision into a right ventricular outflow tract of a patient;
   measuring the diameter of the patient's right ventricular outflow tract,
   cutting from a flat sheet of flexible synthetic resin an ellipse having a major and a minor axis, wherein the minor axis has a predetermined length and is defined by at least two peripheral edges;
   incising said ellipse along the minor axis such that said incision extends along the minor axis for a distance approximately equal to 1.5 times the measured diameter of the patient's right ventricular outflow tract, and is defined by said at least two peripheral edges;
   folding said ellipse in half on itself along said minor axis to form at least two flexible members;
   forming said incision into an orifice of predetermined diameter and shape such that the flexible synthetic resin sheet forms a generally tubular shape with said incision at one end thereof forming an orifice that can open and close when inserted into the patient's right ventricular outflow tract; and
   attaching each of said flexible members to the anterior and posterior wall of the infundibular septum of said right ventricular outflow tract, such that said flexible members are generally parallel to each other, and such that said generally tubular structure is maintained.

9. The method of claim 8, wherein the flexible members are attached to the anterior and posterior wall of the infundibular septum of the right ventricular outflow tract by suturing.

* * * * *